United States Patent
Bernstein

(10) Patent No.: US 6,924,277 B2
(45) Date of Patent: Aug. 2, 2005

(54) CYCLIZED BENZAMIDE NEUROKININ ANTAGONISTS FOR USE IN THERAPY

(75) Inventor: Peter Bernstein, Rose Valley, PA (US)

(73) Assignee: AstraZeneca AB, Sodertalje (SE)

( * ) Notice: Subject to any disclaimer, the term of this patent is extended or adjusted under 35 U.S.C. 154(b) by 132 days.

(21) Appl. No.: 10/381,755

(22) PCT Filed: Sep. 27, 2001

(86) PCT No.: PCT/SE01/02100

§ 371 (c)(1),
(2), (4) Date: Mar. 26, 2003

(87) PCT Pub. No.: WO02/26724

PCT Pub. Date: Apr. 4, 2002

(65) Prior Publication Data

US 2004/0029850 A1 Feb. 12, 2004

(30) Foreign Application Priority Data

Sep. 28, 2000 (SE) .............................................. 0003476

(51) Int. Cl.$^7$ ..................... C07D 273/01; A61K 31/395; A61P 3/04
(52) U.S. Cl. ............. 514/183; 514/211.05; 514/211.06; 514/211.07; 540/455; 540/488; 540/491
(58) Field of Search ................................. 540/455, 488, 540/491; 514/183, 211.05, 211.06, 211.07

(56) References Cited

U.S. PATENT DOCUMENTS

| | | | |
|---|---|---|---|
| 5,525,600 A | 6/1996 | Baudy | |
| 5,541,179 A | 7/1996 | Baudy et al. | |
| 5,789,422 A | 8/1998 | Reichard et al. | |
| 5,998,439 A | 12/1999 | Maynard | |

FOREIGN PATENT DOCUMENTS

| | | | |
|---|---|---|---|
| WO | WO 9628158 | | 9/1996 |
| WO | WO 0064423 | | 11/2000 |
| WO | WO 01/77089 | * | 10/2001 |

OTHER PUBLICATIONS

Swain (Ann. Reports Med. Chem.) 1999.*
Asianian (Ann. Reports Med. Chem.) 2001.*
M. Schuiling et al, ""Role of tachykinin NK1 and NK2 receptors in allergen–induced early and late asthmatic reactions, airway hyperresponsiveness, and airway inflammation in conscious, unrestrained guinea pigs"," Clinica and Experimental Allergy, p. 48–52.

Marie–Ange Coudore–Civiale et al, ""Effect of tachykinin receptor antagonists in experimental neuropathic pain"," European Journal of Pharmacology, p. 175–184, (Mar. 14, 1998).

Ludmilla Mazelin et al., ""Comparative effects of nonpeptide tachykinin receptor antagonists on experimental gut inflammation in rats and guinea–pigs"," Life Sciences, vol. 63 (No. 4), p. 293–304, (Mar. 14, 1998).

D.M. Walsh et al., ""The anxiolytic–like activity of GR159897, a non–peptide NK2 receptor antagonist, in rodent and primate models of anxiety"," Psychopharmacology, p. 186–191, (Mar. 14, 1995).

Raquel M. Teixeira et al., ""Effects of central administration of tachykinin receptor agonists and antagonists on plus–maze behavior in mice"," European Journal of Pharmacology, p. 7–14, (Mar. 14, 1996).

Sharon C. Stratton et al., ""Anxiolytic activity of tachykinin NK2 receptor antagonists in the mouse light–dark box"," European Journal of Pharmacology, p. R11–R12.

* cited by examiner

Primary Examiner—Bruck Kifle

(57) ABSTRACT

Compounds having the general formula

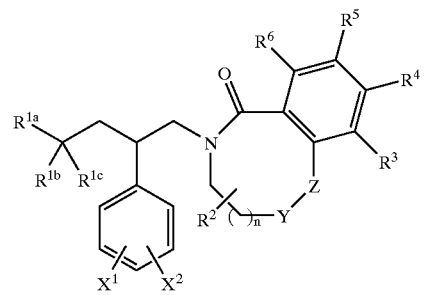

wherein $R^{1a}$, $R^{1b}$, $R^{1c}$, $X^1$, $X^2$, $R^2$, $R^3$, $R^4$, $R^5$, $R^6$, n, Y and Z are as defined in the specification, methods of using such compounds for the treatment of diseases and pharmaceutical composition comprising such compounds.

9 Claims, No Drawings

CYCLIZED BENZAMIDE NEUROKININ ANTAGONISTS FOR USE IN THERAPY

RELATED APPLICATIONS

This is the National Stage of PCT Application No. PCT/SE01/02100, filed Sep. 27, 2001, which claims the benefit under 35 U.S.C. § 119(a–d) of Application No. 0003476-9 filed in Sweden on Sep. 28, 2000.

BACKGROUND

The mammalian neurokinins comprise a class of peptide neurotransmitters which are found in the peripheral and central nervous systems. The three principal neurokinins are Substance P (SP), Neurokinin A (NKA) and Neurokinin B (NKB).

There are also N-terminally extended forms of at least NKA. At least three receptor types are known for the three principal neurokinins. Based upon their relative selectivities favoring the neurokinin agonists SP, NKA and NKB, the receptors are classified as neurokinin 1 ($NK_1$), neurokinin 2 ($NK_2$) and neurokinin 3 ($NK_3$) receptors, respectively.

It is now recognized that anxiety, stress, and depression are interrelated conditions (File S E *Pharmacol, Biochem & Behavior* 54/1:3–12, 1996). Moreover, these complex emotional states cannot be due simply to defects in a single neurotransmitter although 5-HT has been ascribed a principal role (Graeff et al., *Pharmacol, Biochem & Behavior* 54/1: 129–141, 1996). Substance P (SP) was one of the first neuropeptides to be identified in mammalian brain and it is now accepted that all three tachykinins are found within the CNS (Iversen L L *J Psychopharmacol* 3/1: 1–6, 1989), particularly in the striatonigral neurons, hypothalamus and limbic forebrain (ibid). $NK_1$ and $NK_3$ receptors have been identified in the brain as well (Beaujouan et al., *Neurosci*. 18: 857–875, 1986). Controversy has existed regarding the presence of the $NK_2$ receptor in brain, although recent evidence shows receptor localization in at least the septal region (Steinberg et al., *Eur J Neurosci* 10/7:2337–45 1998).

Pharmacological evidence supporting a role for either $NK_1$ or $NK_2$ receptors in anxiety disorders has been accumulating from assorted animal behavioral tests (for examples, see Table 1). Animal models of depression, however, have been used rarely to define the potential utility of NK receptor antagonists. SP stimulates the turnover of other neurotransmitters involved in depression, i.e., 5-HT in the raphe nucleus, an area thought to be linked to depressive phenomena (Forchetti et al., *J. Neurochem*. 38: 1336–1341, 1982). When injected centrally to nuclei responsible for control of emotion and stress, SP evokes a hemodynamic pressor response bridging this peptide to stress induced hypertension (Ku et al., *Peptides*; 19/4:677–82, 1998). Moreover, rises in both heart rate and mean arterial blood pressure evoked by physical stress can be blocked in rodents by centrally administered $NK_1$ receptor antagonists (Culman et al., *J Pharmacol Exp Ther* 280/1:238–46, 1997).

TABLE 1

Neurokinin receptor antagonist activity in behavioral tests of anxiety/depression.

| Author | Cpd (Receptor type) | Behavioral Test | Outcome |
|---|---|---|---|
| Teixeira et al., Eur J Pharmacol 5; 311(1): 7–14, 1996. | $NK_1$ agonists & FK888 ($NK_1$) SR48968 ($NK_2$) | Elevated plus-maze | agonists - anxiogenic antagonists - anxiolytic |
| File Pharm Bio B 58(3): 747–752, 1997. | CGP 49823 ($NK_1$) | Social interaction | anxiolytic |
| Vassout et al Neuropeptides 26/S1: 38, 1994. | CGP 49823 ($NK_1$) | Social interaction test Elevated plus-maze Forced swim test (depression model) | anxiolytic inactive antidepressant (only at 30 mg/kg bid) |
| Stratton et al., Eur. J. Pharmacol. 250: R11–12, 1993. | GR100679 ($NK_2$) SR48968 ($NK_2$) | Light-dark box | anxiolytic |
| Walsh et al., Psychopharmacology 121: 186–191, 1995. | GR159897 ($NK_2$) SR48968 ($NK_2$) | Light-dark box Marmoset human intruder | anxiolytic anxiolytic |

DESCRIPTION

This invention relates to internally cyclized benzamide compounds; to pharmaceutical compositions containing such compounds; as well as to their uses and processes for their preparation. These compounds antagonize the pharmacological actions of the neurokinin 1 ($NK_1$) receptor. These compounds are useful whenever such antagonism is desired. Thus, such compounds are of value in the treatment of those diseases in which Substance P is implicated, for example, in the treatment of major depressive disorder, severe anxiety disorders, stress disorders, major depressive disorder with anxiety, eating disorders, bipolar disorder, substance use disorder, schizophrenic disorders, psychotic disorders, movement disorders, cognitive disorders, depression and/or anxiety, mania or hypomania, aggressive behaviour, obesity, emesis, rheumatoid arthritis, Alzheimer's disease, cancer, oedema, allergic rhinitis, inflammation, pain, gastrointestinal-hypermotility, Huntington's disease, chronic obstructive pulmonary disorder (COPD), hypertension, migraine, bladder hypermotility, or urticaria.

Accordingly, the present invention provides the compounds of the general formula Ia:

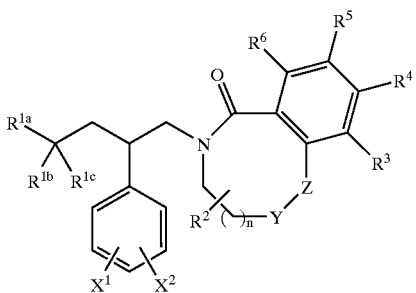

(Ia)

The compounds of the present invention may possess a number of chiral centres, for example at —CH(Ph-X$^1$, X$^2$)—, and at —CH(R$^2$)—. The present invention covers all isomers, diastereoisomers and mixtures thereof that antagonize NK$_1$.

The preferred configuration at —CH(Ph-X$^1$,X$^2$)— is shown in formula (Ib) hereinbelow:

(Ib)

X$^1$ and X$^2$ are independently hydrogen or halo, provided that at least one of X$^1$ or X$^2$ is halo. Favourably, X$^1$ and X$^2$ are both chloro. In a preferred aspect Ph—X$^1$,X$^2$ is 3,4-dichlorophenyl.

R$^{1a}$ is H, NR$^9$R$^{10}$, —OR$^9$,

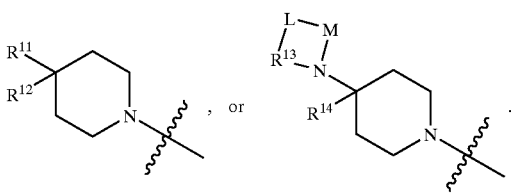

, or

R$^{1b}$ and R$^{1c}$ are independently H or —OR$^9$, or R$^{1b}$ and R$^{1c}$ together are =O, =CH$_2$ or —OCH$_2$CH$_2$O—.

In one embodiment, R$^{1a}$ is H, NR$^9$R$^{10}$ or —OR$^9$. In another embodiment, R$^{1a}$ is

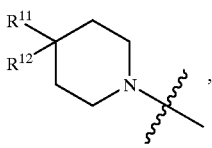

,

R$^{1b}$ is H and R$^{1c}$ is H. And in another embodiment, R$^{1a}$ is

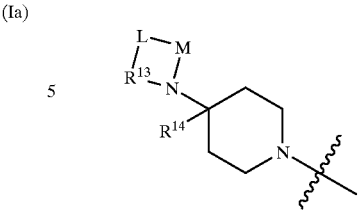

R$^{1b}$ is H and R$^{1c}$ is H.

R$^2$ is H, oxo, —OR$^9$ or —CH$_3$. In one embodiment, R$^2$ is —OR$^9$ or —CH$_3$.

The naphthyl group of Ia is an optionally substituted naphth-1-yl. Suitable substituents, which are optional, for the naphth-1-yl group include hydroxy; cyano; nitro; trifluoromethoxy; trifluoromethyl; C$_{1-6}$alkylsulfonyl for example methylsulphonyl; halo for example chloro, bromo, fluoro or iodo; C$_{1-6}$alkoxy for example methoxy, ethoxy or propoxy; methylenedioxy (—OCH$_2$O—), C$_{1-6}$alkyl for example methyl or ethyl; C$_{2-6}$alkenyl for example ethenyl, prop-1-enyl or prop-2-enyl; C$_{2-6}$alkynyl for example ethynyl; carboxy, C$_{1-6}$alkoxycarbonyl for example methoxycarbonyl; carbamoyl; C$_{1-6}$alkylcarbamoyl for example methylcarbamoyl or ethylcarbamoyl; di-C$_{1-6}$alkylcarbamoyl for example di-methylcarbamoyl; C$_{1-6}$alkanoyl for example acetyl or propionyl; C$_{1-6}$alkanoylamino for example acetylamino or propionylamino; aminosulfonyl; and C$_{1-6}$alkyl for example methyl substituted by any of the hereinabove substituents.

Favourably the naphth-1-yl group is unsubstituted or is substituted by up to three substituents. Preferred substituents for the naphth-1-yl group include cyano; nitro; C$_{1-6}$alkylsulfonyl for example methylsulphonyl; halo for example chloro, bromo, fluoro or iodo; C$_{1-6}$alkoxy for example methoxy, ethoxy, n-propoxy or isopropoxy; methylenedioxy (—OCH$_2$O—); C$_{1-6}$alkyl for example methyl or ethyl; C$_{2-6}$alkenyl for example prop-2-enyl; C$_{2-6}$alkynyl for example ethynyl; carboxy, carbamoyl; C$_{1-6}$alkyl-carbamoyl for example methylcarbamoyl; di-C$_{1-6}$alkylcarbamoyl for example di-methylcarbamoyl; C$_{1-6}$alkanoyl for example acetyl; C$_{1-6}$alkanoylamino for example acetylamino; aminosulfonyl; and cyanoC$_{1-6}$alkyl for example cyanomethyl.

More preferred substituents for the naphth-1-yl group are cyano, methoxy, ethoxy, isopropoxy, fluoro, bromo, chloro, iodo, nitro, cyanomethyl, carboxy, carbamoyl, ethynyl, methyl, ethyl, dimethylcarbamoyl, methylsulfonyl, aminosulfonyl, prop-2-enyl, acetyl and acetylamino.

In particular the naphth-1-yl group may be substituted by up to three substituents selected from cyano, methoxy, ethyl, fluoro and nitro.

R$^3$, R$^4$, R$^5$ and R$^6$ are each independently selected from H, cyano, nitro, trifluoromethoxy, trifluoromethyl, C$_{1-6}$alkylsulfonyl, halo, —OR$^9$, —OCH$_2$O—, C$_{1-6}$alkyl, C$_{2-6}$alkenyl, C$_{2-6}$alkynyl, —C(=O)OR$^9$, —C(=O)NR$^9$, R$^{10}$, —OC(=O)R$^9$, —NR$^9$C(=O)R$^{10}$, aminosulfonyl and C$_{1-6}$alkyl substituted by any of the hereinabove substituents; wherein at least one of R$^3$, R$^4$, R$^5$ and R$^6$ are H.

In one embodiment, R$^3$, R$^4$, R$^5$ and R$^6$ are selected from H, cyano, nitro, —S(=O)C$_{1-6}$alkyl, halo, —OR$^9$, —OCH$_2$O—, C$_{1-6}$alkyl, C$_{2-6}$alkenyl, C$_{2-6}$alkynyl, —C(=O)OR$^9$, —C(=O)NR$^9$R$^{10}$, —OC(=O)R$^9$, —NR$^9$C (=O)R$^{10}$, aminosulfonyl and —C$_{1-6}$alkylcyano; wherein at least two of R$^3$, R$^4$, R$^5$ and R$^6$ are H.

In another embodiment, R$^3$, R$^4$, R$^5$ and R$^6$ are selected from H, cyano, methoxy, ethoxy, isopropoxy, fluoro, bromo, chloro, iodo, nitro, cyanomethyl, carboxy, carbamoyl, ethynyl, methyl, ethyl, dimethylcarbamoyl, methylsulfonyl, aminosulfonyl, prop-2-enyl, acetyl and acetylamino; wherein at least three of R$^3$, R$^4$, R$^5$ and R$^6$ are H.

In another embodiment, R$^3$, R$^4$, R$^5$ and R$^6$ are selected from H, cyano, methoxy, ethyl, fluoro and nitro; wherein at least two of R$^3$, R$^4$, R$^5$ and R$^6$ are H.

R$^{11}$ is phenyl, substituted in at least the ortho position by C$_{1-6}$alkylthio, C$_{1-6}$alkylsulfinyl, C$_{1-6}$alkylsulfonyl, trifluoromethylthio, trifluoromethylsulfinyl, C$_{1-6}$alkanesulfunamido, C$_{1-6}$alkanoyl, C$_{1-6}$alkoxy-carbonyl, succinamido, carbamoyl, C$_{1-6}$alkylcarbamoyl, di-C$_{1-6}$alkylcarbamoyl, C$_{1-6}$alkoxy-C$_{1-6}$alkylcarbamoyl, N-methylcarbamoyl, C$_{1-6}$alkanoylamino, ureido, C$_{1-6}$ureido, di-C$_{1-6}$alkylureido, amino, C$_{1-6}$alkylamino, or di-C$_{1-6}$alkylamino.

R$^{12}$ is selected from hydrogen, hydroxy, C$_{1-6}$alkoxy, C$_{1-6}$alkanoyloxy, C$_{1-6}$alkanoyl, C$_{1-6}$alkoxycarbonyl, C$_{1-6}$alkanoylamino, C$_{1-6}$alkyl, carbamoyl, C$_{1-6}$alkylcarbamoyl and bis(C$_{1-6}$alkyl)carbamoyl.

R$^{13}$ is —CH$_2$CH$_2$—, —CH$_2$CH$_2$CH$_2$— or —CH$_2$CH$_2$CH$_2$CH$_2$—.

R$^{14}$ is hydrogen, hydroxy, C$_{1-6}$alkoxy, C$_{1-6}$alkanoyloxy, C$_{1-6}$alkanoyl, C$_{1-6}$alkoxycarbonyl, C$_{1-6}$alkanoylamino, C$_{1-6}$alkyl, carbamoyl, C$_{1-6}$alkylcarbamoyl or di-C$_{1-6}$alkylcarbamoyl.

M is —C(=O)— or —S(=O)$_2$—,

L is —NH— or —CH$_2$—.

Y and Z are CH$_2$ or O, wherein Y does not equal Z.

n is 0 or 1.

Another aspect of the invention involves a pharmaceutical composition comprising a therapeutically effective amound of a compound of formula Ia.

Another aspect of the invention involves a method of treating major depressive disorder, severe anxiety disorders, stress disorders, major depressive disorder with anxiety, eating disorders, bipolar disorder, substance use disorder, schizophrenic disorders, psychotic disorders, movement disorders, cognitive disorders, depression and/or anxiety, mania or hypomania, aggressive behaviour, obesity, emesis, rheumatoid arthritis, Alzheimer's disease, cancer, oedema, allergic rhinitis, inflammation, pain, gastrointestinal-hypermotility, Huntington's disease, COPD, hypertension, migraine, bladder hypermotility, or urticaria comprising administering an effective amount of an NK1 antagonist of formula Ia.

Particular compounds of this invention are provided as the Examples hereinbelow.

C$_{Y-Z}$alkyl, unless otherwise specified, means an alkyl chain containing a minimum Y total carbon atoms and a maximum Z total carbon atoms. These alkyl chains may be branched or unbranched, cyclic, acyclic or a combination of cyclic and acyclic. For example, the following substituents would be included in the general description "C$_{4-7}$alkyl":

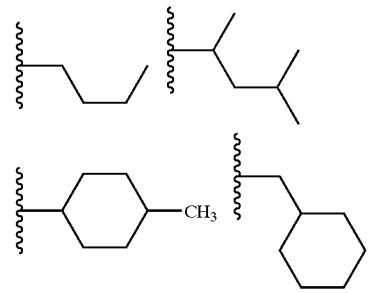

Pharmaceutically-acceptable salts may be prepared from the corresponding acid in conventional manner. Non-pharmaceutically-acceptable salts may be useful as intermediates and as such are another aspect of the present invention.

The symbol "=O" means a double bonded oxygen, and when this symbol is used attached to a carbon it forms a carbonyl group.

Some of the compounds of the present invention are capable of forming salts with various inorganic and organic acids and bases and such salts are also within the scope of this invention. Examples of such acid addition salts include acetate, adipate, ascorbate, benzoate, benzenesulfonate, bisulfate, butyrate, camphorate, camphorsulfonate, citrate, cyclohexyl sulfamate, ethanesulfonate, fumarate, glutamate, glycolate, hemisulfate, 2-hydroxyethylsulfonate, heptanoate, hexanoate, hydrochloride, hydrobromide, hydroiodide, hydroxymaleate, lactate, malate, maleate, methanesulfonate, 2-naphthalenesulfonate, nitrate, oxalate, pamoate, persulfate, phenylacetate, phosphate, picrate, pivalate, propionate, quinate, salicylate, stearate, succinate, sulfamate, sulfanilate, sulfate, tartrate, tosylate (p-toluenesulfonate), and undecanoate. Base salts include ammonium salts, alkali metal salts such as sodium, lithium and potassium salts, alkaline earth metal salts such as aluminum, calcium and magnesium salts, salts with organic bases such as dicyclohexylamine salts, N-methyl-D-glucamine, and salts with amino acids such as arginine, lysine, ornithine, and so forth. Also, basic nitrogen-containing groups may be quaternized with such agents as: lower alkyl halides, such as methyl, ethyl, propyl, and butyl halides; dialkyl sulfates like dimethyl, diethyl, dibutyl; diamyl sulfates; long chain halides such as decyl, lauryl, myristyl and stearyl halides; aralkyl halides like benzyl bromide and others. Non-toxic physiologically-acceptable salts are preferred, although other salts are also useful, such as in isolating or purifying the product.

The salts may be formed by conventional means, such as by reacting the free base form of the product with one or more equivalents of the appropriate acid in a solvent or medium in which the salt is insoluble, or in a solvent such as water, which is removed in vacuo or by freeze drying or by exchanging the anions of an existing salt for another anion on a suitable ion-exchange resin.

In order to use a compound of the formula (I) or a pharmaceutically acceptable salt thereof for the therapeutic treatment (including prophylactic treatment) of mammals including humans, it is normally formulated in accordance with standard pharmaceutical practice as a pharmaceutical composition.

Therefore in another aspect the present invention provides a pharmaceutical composition which comprises a compound of the formula (I) or a pharmaceutically acceptable salt and pharmaceutically acceptable carrier.

The pharmaceutical compositions of this invention may be administered in standard manner for the disease condition that it is desired to treat, for example by oral, topical, parenteral, buccal, nasal, vaginal or rectal administration or by inhalation or insufflation. For these purposes the compounds of this invention may be formulated by means known in the art into the form of, for example, tablets, capsules, aqueous or oily solutions, suspensions, emulsions, creams, ointments, gels, nasal sprays, suppositories, finely divided powders or aerosols or nebulisers for inhalation, and for parenteral use (including intravenous, intramuscular or infusion) sterile aqueous or oily solutions or suspensions or sterile emulsions.

In addition to the compounds of the present invention the pharmaceutical composition of this invention may also contain, or be co-administered (simultaneously or sequentially) with, one or more pharmacological agents of value in treating one or more disease conditions referred to herein.

The pharmaceutical compositions of this invention will normally be administered to humans so that, for example, a daily dose of 0.01 to 25 mg/kg body weight (and preferably of 0.1 to 5 mg/kg body weight) is received. This daily dose may be given in divided doses as necessary, the precise amount of the compound received and the route of administration depending on the weight, age and sex of the patient being treated and on the particular disease Typically unit dosage forms will contain about 1 mg to 500 mg of a compound of this invention. For example a tablet or capsule for oral administration may conveniently contain up to 250 mg (and typically 5 to 100 mg) of a compound of the formula (I) or a pharmaceutically acceptable salt thereof. In another example, for administration by inhalation, a compound of the formula (I) or a pharmaceutically acceptable salt thereof may be administered in a daily dosage range of 5 to 100 mg, in a single dose or divided into two to four daily doses. In a further example, for administration by intravenous or intramuscular injection or infusion, a sterile solution or suspension containing up to 10% w/w (and typically 5% w/w) of a compound of the formula (I) or a pharmaceutically acceptable salt thereof may be used.

Therefore in a further aspect, the present invention provides a compound of the formula (I) or a pharmaceutically acceptable salt thereof for use in a method of therapeutic treatment of the human or animal body.

In yet a further aspect the present invention provides a method of treating a disease condition wherein antagonism of the $NK_1$ receptor is beneficial which comprises administering to a warm-blooded animal an effective amount of a compound of the formula (I) or a pharmaceutically-acceptable salt thereof. The present invention also provides the use of a compound of the formula (I) or a pharmaceutically acceptable salt thereof in the preparation of a medicament for use in a disease condition wherein antagonism of the $NK_1$ receptor is beneficial.

The compounds of the formula (I) and their pharmaceutically acceptable salts may be made by processes as described and exemplified herein and by processes similar thereto and by processes known in the chemical art. If not commercially available, starting materials for these processes may be made by procedures which are selected from the chemical art using techniques which are similar or analogous to the synthesis of known compounds.

It is well known in the art how to prepare optically-active forms (for example, by resolution of the racemic form or by synthesis from optically-active starting materials) and how to determine the $NK_1$ antagonist properties by the standard tests known in the art and those described hereinafter.

Some individual compounds within the scope of this invention may contain double bonds. Representations of double bonds in this invention are meant to include both the E and the Z isomer of the double bond. Additionally, some species within the scope of this invention may contain one or more asymmetric centers. This invention includes the use of any of the optically pure stereoisomers as well as any combination of stereoisomers.

The following biological test methods, data and Examples serve to illustrate and further describe the invention.

The utility of a compound of the invention or a pharmaceutically acceptable salt thereof (hereinafter, collectively referred to as a "compound") may be demonstrated by standard tests and clinical studies, including those disclosed in the publications described below.

SP Receptor Binding Assay (Test A)

The ability of a compound of the invention to antagonize the binding of SP at the $NK_1$ receptor may be demonstrated using an assay using the human $NK_1$ receptor expressed in Mouse Erythroleukemia (MEL) cells. The human $NK_1$ receptor was isolated and characterized as described in: B. Hopkins, et al. "Isolation and characterization of the human lung $NK_1$ receptor cDNA" *Biochem. Biophys. Res. Comm.*, 1991, 180, 1110–1117; and the $NK_1$ receptor was expressed in Mouse Erythroleukemia (MEL) cells using a procedure similar to that described in Test B below.

Neurokinin A (NKA) Receptor Binding Assay (Test B)

The ability of a compound of the invention to antagonize the binding of NKA at the $NK_2$ receptor may be demonstrated using an assay using the human $NK_2$ receptor expressed in Mouse Erythroleukemia (MEL) cells, as described in: Aharony, D., et al. "Isolation and Pharmacological Characterization of a Hampster Neurokinin A Receptor cDNA" *Molecular Pharmacology*, 1994, 45, 9–19.

The selectivity of a compound for binding at the $NK_1$ and the $NK_2$ receptors may be shown by determining its binding at other receptors using standard assays, for example, one using a tritiated derivative of NKB in a tissue preparation selective for $NK_3$ receptors. In general, the compounds of the invention which were tested demonstrated statistically significant binding activity in Test A and Test B with a $K_i$ of 1 mM or much less typically being measured.

Rabbit Pulmonary Artery: $NK_1$ In Vitro Functional Assay (Test C)

The ability of a compound of the invention to antagonize the action of the agonist Ac-[$Arg^6$, $Sar^9$, $Met(O_2)^{11}$] Substance P (6-11), ASMSP, in a pulmonary tissue may be demonstrated as follows.

Male New Zealand white rabbits are euthanized via i.v. injection into the ear vein with 60 mg/kg Nembutal (50 mg/mL). Preceding the Nembutal into the vein is Heparin (1000 units/mL) at 0.0025 mL/kg for anticoagulant purposes. The chest cavity is opened from the top of the rib cage to the sternum and the heart, lungs and part of the trachea are removed. The pulmonary arteries are isolated from the rest of the tissues and cut in half to serve as pairs.

The segments are suspended between stainless steel stirrups, so as not to remove any of the endothelium, and placed in water-jacketed (37.0° C.) tissue baths containing physiological salt solution of the following composition (mM): NaCl, 118.0; KCl, 4.7; $CaCl_2$, 1.8; $MgCl_2$, 0.54; $NaH_2PO_4$, 1.0; $NaHCO_3$, 25.0; glucose, 11.0; indomethacin, 0.005 (to inhibit cyclooxygenase); and dl-Propranolol, 0.001 (to block β receptors); gassed continuously with 95% $O_2$-5% $CO_2$. Responses are measured on a Grass polygraph via Grass FT-03 transducers.

Initial tension placed on each tissue is 2 grams, which is maintained throughout the 1.0 hour equilibration period. Tissues are washed with the physiological salt solution at 15 minute intervals. At the 30 and 45 minute wash the following treatments are added: $1\times10^{-6}$ M Thiorphan (to block E.C.3.4.24.11), $3\times10^{-8}$ M (S)-N-[2-(3,4-dichlorophenyl)-4-[4-(2-oxoperhydropyrimidin-1-yl)piperidino]butyl]-N-methylbenzamide (to block $NK_2$ receptors), and the given concentration of the compound being tested. At the end of the 1.0 h equilibration, $3\times10^{-6}$ M phenylephrine hydrochloride is added for 1.0 h. At the end of 1.0 h, a dose relaxation curve to ASMSP is done. Each tissue is treated as a individual and is considered finished when it fails to relax further for 2 consecutive doses. When a tissue is complete, $1\times10^{-3}$ M Papaverine is added for maximum relaxation.

Percent inhibition is determined when a tested compound produces a statistically significant (p<0.05) reduction of the total relaxation which is calculated using the total relaxation of the Papaverine as 100%. Potencies of the compounds are determined by calculating the apparent dissociation constants ($K_B$) for each concentration tested using the standard equation:

$$KB=[\text{antagonist}]/(\text{dose ratio}-1)$$

where dose ratio=antilog[(agonist–log molar $EC_{50}$ without compound)–(–log molar $EC_{50}$ with compound)]. The $K_B$ values may be converted to the negative logarithms and expressed as –log molar KB (i.e. $pK_B$). For this evaluation, complete concentration-response curves for agonist obtained in the absence and presence of the compound tested using paired pulmonary artery rings. The potency of the agonist is determined at 50% of its own maximum relaxation in each curve. The $EC_{50}$ values are converted to negative logarithms and expressed as –log molar $EC_{50}$.

$NK_2$ In Vitro Functional Assay (Test D)

The ability of a compound of the invention to antagonize the action of the agonist [β-ala8] NKA (4-10), BANK, in a pulmonary tissue may be demonstrated as follows. Male New Zealand white rabbits are euthanized via i.v. injection into the ear vein with 60 mg/kg Nembutal (50 mg/mL). Preceding the Nembutal into the vein is Heparin (1000 units/mL) at 0.0025 mL/kg for anticoagulant purposes. The chest cavity is opened from the top of the rib cage to the sternum and a small incision is made into the heart so that the left and right pulmonary arteries can be cannulated with polyethylene tubing (PE260 and PE190 respectively). The pulmonary arteries are isolated from the rest of the tissues, then rubbed over an intimal surface to remove the endothelium, and cut in half to serve as pairs. The segments are suspended between stainless steel stirrups and placed in water-jacketed (37.0° C.) tissue baths containing physiological salt solution of the following composition (mM): NaCl, 118.0; KCl, 4.7; $CaCl_2$, 1.8; $MgCl_2$, 0.54; $NaH_2PO_4$, 1.0; $NaHCO_3$, 25.0; glucose, 11.0; and indomethacin, 0.005 (to inhibit cyclooxygenase); gassed continuously with 95% $O_2$-5% $CO_2$. Responses are measured on a Grass polygraph via Grass FT-03 transducers.

Initial tension placed on each tissue is 2 g, which is maintained throughout the 45 min equilibration period. Tissues are washed with the physiological salt solution at 15 min intervals. After the 45 min equilibration period, $3\times10^{-2}$ M KCl is given for 60 min to test the viability of the tissues. The tissues are then washed extensively for 30 min. The concentration of the compound being tested is then added for 30 min. At the end of the 30 min, a cumulative dose response curve to BANK is performed. Each tissue is treated as a individual and is considered finished when it fails to contract further for 2 consecutive doses. When a tissue is complete, $3\times10^{-2}$ M $BaCl_2$ is added for maximum contraction.

Percent inhibition is determined when a tested compound produces a statistically significant (p<0.05) reduction of the total contraction which is calculated using the total contraction of the $BaCl_2$ as 100%. Potencies of the compounds are determined by calculating the apparent dissociation constants ($K_B$) for each concentration tested using the standard equation:

$$K_B=[\text{antagonist}]/(\text{dose ratio}-1)$$

where dose ratio=antilog[(agonist–log molar $EC_{50}$ without compound)–(–log molar $EC_{50}$ with compound)]. The $K_B$ values may be converted to the negative logarithms and expressed as –log molar $K_B$ (i.e. $pK_B$). For this evaluation, complete concentration-response curves for agonist obtained in the absence and presence of the compound tested using paired pulmonary artery rings. The potency of the agonist is determined at 50% of its own maximum relaxation in each curve. The $EC_{50}$ values are converted to negative logarithms and expressed as –log molar $EC_{50}$.

$NK_1$ and $NK_2$ In Vivo Functional Assay (Test E)

The activity of a compound as an antagonist of $NK_1$ and/or $NK_2$ receptors also may be demonstrated in vivo in laboratory animals as described in: Buckner et al. "Differential Blockade by Tachykinin $NK_1$ and $NK_2$ Receptor Antagonists of Bronchoconstriction Induced by Direct-Acting Agonists and the Indirect-Acting Mimetics Capsaicin, Serotonin and 2-Methyl-Serotonin in the Anesthetized Guinea Pig." *J. Pharm. Exp. Ther.*, 1993, Vol 267(3), pp.1168–1175. The assay is carried out as follows.

Compounds are tested in anesthetized guinea pigs pretreated with i.v. indomethacin (10 mg/kg, 20 min), propranolol (0.5 mg/kg, 15 min), and thiorphan (10 mg/kg, 10 min).

Antagonists or vehicle are administered i.v. and orally, 30 and 120 min prior to increasing concentrations of agonist, respectively. The agonists used in these studies are ASMSP (Ac-[$Arg^6$, $Sar^9$, $Met(O_2)^{11}$]-SP(6-11)) and BANK (β-ala-8 NKA4-10).

Administered i.v., ASMSP is selective for $NK_1$ receptors, and BANK is selective for $NK_2$ receptors. Maximum response is defined as zero conductance ($G_L$, 1/Rp). $ED_{50}$ values are calculated (the dose of agonist resulting in a reduction of $G_L$ to 50% of baseline), and converted to the negative logarithm ($-\log ED_{50}$). The $ED_{50}$ values, obtained in the presence (P) and absence (A) of antagonist, are used to calculate a Dose Ratio (P/A), an expression of potency. Data are expressed as mean±SEM and statistical differences were determined using ANOVA/Tukey-Kramer and Student's t-test, with $p<0.05$ considered statistically significant.

Compounds of the present invention exhibit marked activity in the foregoing tests and are considered useful for the treatment of those diseases in which the $NK_1$ and/or $NK_2$ receptor is implicated, for example, in the treatment of asthma and related conditions.

EXAMPLES

The invention will now be illustrated by the following non-limiting examples, in which, unless stated otherwise:

(i) temperatures are given in degrees Celsius (°C.); unless otherwise stated, operations were carried out at room or ambient temperature, that is, at a temperature in the range of 18–25° C.;

(ii) organic solutions were dried over anhydrous magnesium sulfate or anhydrous sodium sulfate; evaporation of solvent was carried out using a rotary evaporator under reduced pressure (600–4000 Pascals; 4.5–30 mm Hg) with a bath temperature of up to 60° C.;

(iii) chromatography means flash chromatography on silica gel; thin layer chromatography (TLC) was carried out on silica gel plates;

(iv) in general, the course of reactions was followed by TLC or HPLC and reaction times are given for illustration only;

(v) melting points are uncorrected and (dec) indicates decomposition;

(vi) final products had satisfactory proton nuclear magnetic resonance (NMR) spectra;

(vii) when given, NMR data is in the form of delta values for major diagnostic protons, given in parts per million (ppm) relative to tetramethylsilane (TMS) as an internal standard, determined at 300 MHz using deuterated chloroform ($CDCl_3$) as solvent; conventional abbreviations for signal shape are used; for AB spectra the directly observed shifts are reported; coupling constants (J) are given in Hz; Ar designates an aromatic proton when such an assignment is made;

(viii) reduced pressures are given as absolute pressures in pascals (Pa); elevated pressures are given as gauge pressures in bars;

(ix) non-aqueous reactions were run under a nitrogen atmosphere (x) solvent ratios are given in volume:volume (v/v) terms; and (xi) Mass spectra (MS) were run using an automated system with atmospheric pressure chemical ionization (APCI). Generally, only spectra where parent masses are observed are reported. The lowest mass major ion is reported for molecules where isotope splitting results in multiple mass spectral peaks (for example when chlorine is present).

Terms and Abbreviations: Solvent mixture compositions are given as volume percentages or volume ratios. In cases were the NMR spectra are complex, only diagnostic signals are reported. DCM, methylene chloride, DMF; N,N-dimethylformamide, $Et_2O$; diethyl ether, EtOAc; ethyl acetate, HOAc; acetic acid, iPrOH; isopropanol, h; hour(s), min; minutes, NMR; nuclear magnetic resonance, MeOH; methanol, RT; room temperature, sat.; saturated, THF; tetrahydrofuran.

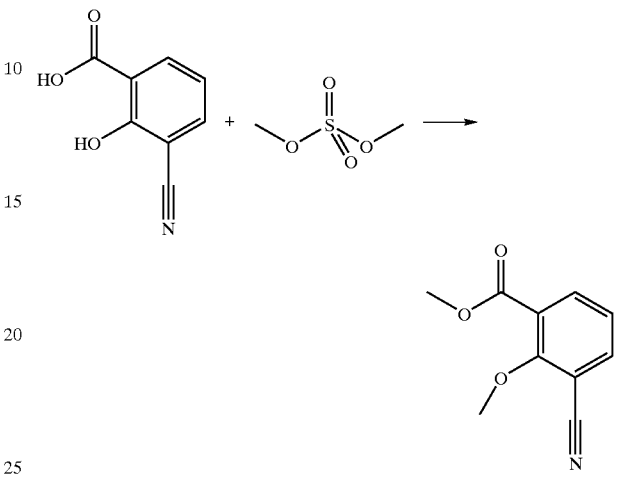

Methyl 3-cyano-2-methoxybenzoate. A stirred mixture of 3-cyano-2-hydroxybenzoic acid (prepared as described in DE 2749518) (2.94 g, 18.1 mmol), dimethylsulfate (9.11 g, 72.2 mmol), potassium carbonate (9.98 g, 72.2 mmol) and acetone (40 mL) was heated at reflux for 2.5 hr. The cooled mixture was filtered through a pad of Celite® and the solvent removed from the filtrate in vacuo to yield a pale yellow solid. The solid dissolved in EtOAc was washed with dilute HCl, sat. $NaHCO_3$ and brine; dried ($Na_2SO_4$), filtered and the solvent removed in vacuo. Chromatography of the pale yellow solid through a 10 g Mega Bond Elut® column using DCM as eluent gave the title compound as a white solid; 3.28 g (95%). $^1H$ NMR (300 MHz, DMSO-$d_6$) δ 8.04–8.06 (m, 1H), 8.02–8.04 (m, 1H), 7.41 (t, 1H), 3.96 (s, 3H), 3.38 (s, 3H). MS APCI, m/z=192 (M+1).

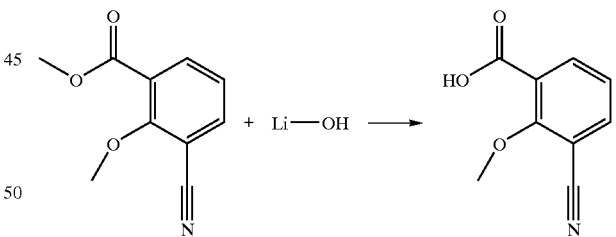

3-Cyano-2-methoxybenzoic Acid. A stirred solution of methyl 3-cyano-2-methoxybenzoate (3.28 g, 17.2 mmol), lithium hydroxide hydrate (1.08 g, 25.8 mmol) in a mixture of THF (20 mL), water (8 mL) and MeOH (8 mL) was rapidly heated to a gentle reflux for 5 min and allowed to stir at ambient temperature for an additional 10 min. The mixture was then poured into water (30 mL) and sat. $NaHCO_3$ (5 mL) and extracted with $Et_2O$ (50 mL). The aqueous phase was acidified to pH 2 with 1N HCl and the resulting white precipitate was extracted with EtOAc (60 mL). The EtOAc extract was washed with brine, dried ($Na_2SO_4$), filtered and the solvent stripped in vacuo. The solid was twice treated with MeOH (15 mL) and toluene (30 mL) and the solvent stripped in vacuo to yield the title compound as a white solid; 2.89 g (95%). ¹H NMR (300 MHz, DMSO-d₆) δ 13.48 (br.s, 1H), 7.98–8.03 (m, 2H), 7.38 (t, 1H), 3.96 (s, 3H).

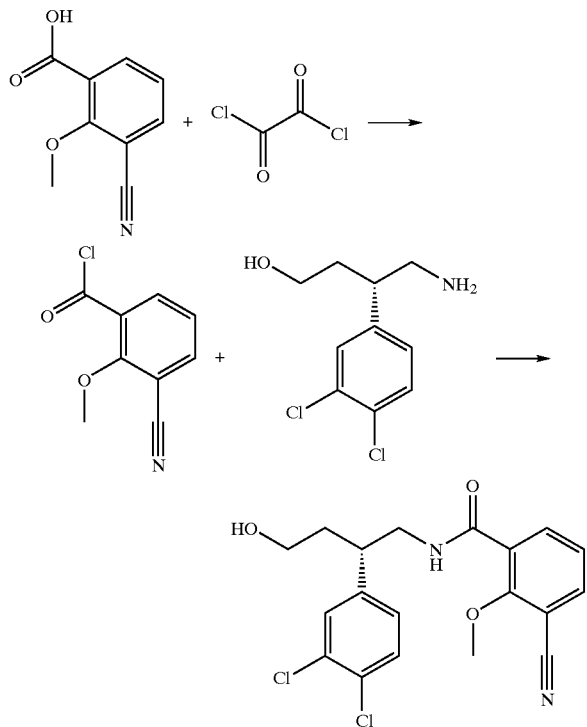

N-[2-(S)-(3,4-Dichlorophenyl)-4-hydroxybutyl]-3-cyano-2-methoxybenzamide. A stirred suspension of 3-cyano-2-methoxybenzoic acid (2.9 g, 16.3 mmol) and oxalyl chloride (2.5 g, 19.5 mmol) in DCM (25 mL) was treated with DMF (10 µL) and bubbling was observed. The suspension became a clear solution after 1 hr. After 90 min the solvent was evaporated to yield an off-white solid. The solid was dissolved in 15 mL DCM, cooled to 0° C. and a suspension of 2-(S)-3,4-(dichlorophenyl)-4-hydroxybutanamine (S. C. Miller; WO 9410146) (4.2 g, 17.9 mmol) and 10 mL DCM was added in 1 portion. 1N NaOH solution (25 mL) was then added and the solution stirred rapidly for 30 min. The solution was acidified with 1N HCl and extracted with EtOAc. The EtOAc extract was washed with brine, dried (Na₂SO₄), filtered and the solvent removed in vacuo to yield a pale yellow viscous oil. Chromatography with DCM and 2%, 4%, 6% MeOH in DCM as eluent gave the title compound as a pale yellow oil-foam which was dried under high vacuum; 6.5 g (quantitative). ¹H NMR (300 MHz, DMSO-d₆) δ 8.43 (t, 1H), 7.85 (dd, 1H), 7.53–7.59 (m, 3H), 7.25–7.31 (m, 2H), 3.75 (s, 3H), 3.28–3.53 (m, 6H), 1.82–1.93 (m, 1H), 1.64–1.76 (m, 1H). MS APCI, m/z=393 (M+1).

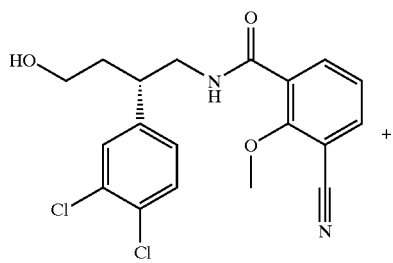

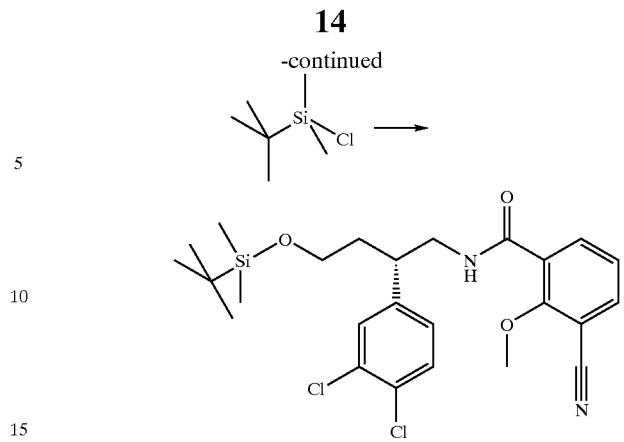

N-[4-(tert-Butyldimethylsilanyloxy)-2-(S)-(3,4-dichlorophenyl)butyl]-3-cyano-2-methoxybenzamide. To a stirred solution of N-[2-(S)-(3,4-dichlorophenyl)-4-hydroxybutyl]-3-cyano-2-methoxybenzamide (6.5 g, 16.7 mmol) and tert-butyldimethylsilyl chloride (3.78 g, 25 mmol) in DCM (30 mL) was added 4-(dimethylamino)pyridine (0.1 g, 0.8 mmol) and triethylamine (2.7 g, 26.7 mmol). After ~2 min a haze was observed above the solvent and 15 mL additional DCM was added to aid stirring. The solution was allowed to stir over a weekend. The reaction mixture was poured into a separatory funnel, diluted with water, DCM and 50 mL sat. NaHCO₃ solution. The collected DCM layer was washed with 1M HOAc (50 mL), sat. NaHCO₃ solution (100 mL), dried (Na₂SO₄), filtered and the solvent removed in vacuo to yield a pale yellow clear oil. Chromatography with DCM as eluent yielded the title compound as a pale yellow oil, 8.2 g (97%). ¹H NMR (300 MHz, DMSO-d₆) δ 8.49 (t, 1H), 7.89 (dd, 1H), 7.55–7.63 (m, 3H), 7.29–7.35 (m, 2H), 3.77 (s, 3H), 3.10–3.58 (m, 7H), 0.87 (s, 9H), 0.00 (s, 3H), −0.02 (s, 3H). MS APCI, m/z=507 (M+1).

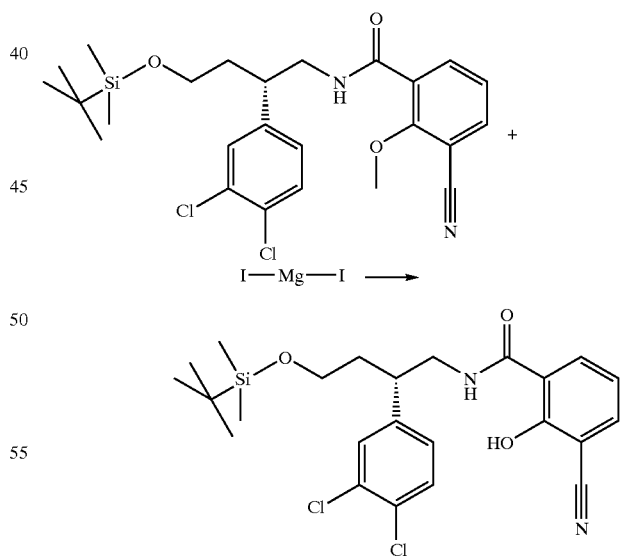

N-[4-(tert-Butyldimethylsilanyloxy)-2-(S)(3,4-dichlorophenyl)butyl]-3-cyano-2-hydroxybenzamide. Magnesium iodide etherate was prepared from magnesium metal (1.02 g, 41 mmol) and iodine (5.3 g, 21 mmol) in ether and added, via cannula, to N-[4-(tert-butyldimethylsilanyloxy)-2-(S)(3,4-dichlorophenyl)butyl]-3-cyano-2-methoxybenzamide (8.2 g, 16.2 mmol) dissolved in 20 mL dry benzene. Upon addition, the solution turned progressively yellower. The mixture was heated at reflux for 5 hr, cooled to RT and quenched with 50 mL ~1M HOAc. DCM was added and the mixture was transferred to a separatory funnel. The separated DCM phase was dried (MgSO₄), filtered, and the solvent removed in vacuo to yield a very pale yellow solid. Chromatography with DCM and 2% MeOH in DCM as eluent gave the title compound as a white solid, 7.02 g (88%). ¹H NMR (300 MHz, DMSO-d₆) δ 14.18 (s, 1H), 9.28 (t, 1H), 8.13 (dd, 1H), 7.95 (d, 1H), 7.59–7.63 (m, 2H), 7.31 (dd, 1H), 7.11 (t, 1H), 3.20–3.65 (m, 6H), 2.58 (br. s, 1H), 0.88 (s, 9H), 0.01 (s, 3H), 0.00 (s, 3H). MS APCI, m/z =493 (M+1).

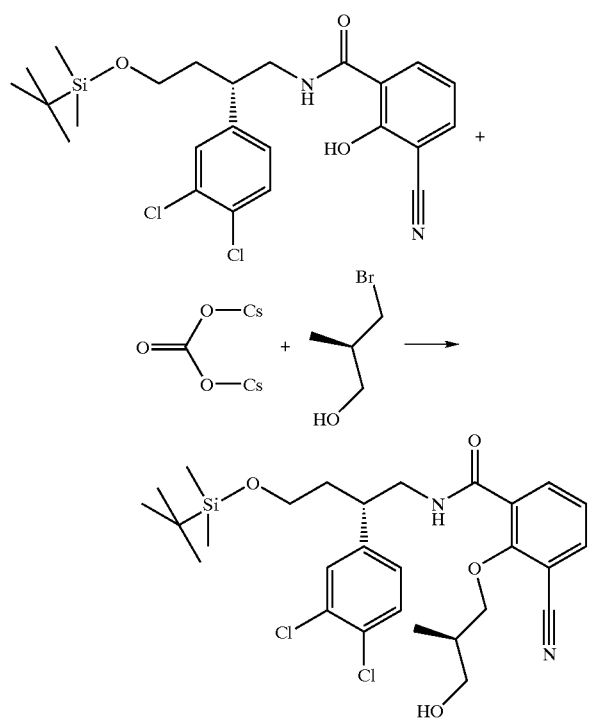

N-[4(tert-Butyldimethylsilanyloxy)-2-(S)-(3,4-dichlorophenyl)butyl]-3-cyano-2-(3-hydroxy-2-(R)-methylpropoxy)benzamide. A stirred mixture of cesium carbonate (5.08 g, 15.6 mmol), N-[4-(tert-butyldimethylsilanyloxy)-2-(S)-(3,4-dichlorophenyl)butyl]-3-cyano-2-hydroxybenzamide (5.90 g, 12.0 mmol) and 5 ml of dry DMF was heated at 65° for 15 min and (R)-(–)-3-bromo-2-methyl-1-propanol (4.04 g, 26.4 mmol) was added dropwise over 5 min. The oil bath was raised to 110° C. and the mixture stirred overnight. The cooled mixture was poured into 1 L of water containing 50 mL of sat NaCl and extracted with 250 mL and 200 mL portions of DCM. The combined extracts were washed with 500 mL of water, dried (Na₂SO₄), filtered and the solvent removed in vacuo. The residue was chromatographed using 25%, 35% and 50% EtOAc/hexane as eluent to yield 2.90 g (49% recovered starting material) and 2.67 g (40%) of the title compound.

The above reaction repeated twice on sequentially recovered starting material yielded 1.06 g (32%) and 0.61 g (31%) of additional title compound. Total yield was 4.34 g (64%) of white solid. ¹H NMR (300 MHz, CDCl₃) δ 8.23 (dd, 1H), 7.71 (dd, 1H), 7.59 (m, 1H), 7.41 (d, 1H), 7.27–7.35 (m, 2H), 7.10 (dd, 1H), 4.02–4.14 (m, 2H), 3.39–3.88 (m, 6H), 3.11–3.21 (m, 1H), 2.19–2.22 (m, 1H), 1.95–2.06 (m, 2H), 1.72–1.81 (m, 1H), 0.94–1.05 (m, 3H), 0.87 (s, 9H), 0.00 (s, 6H)

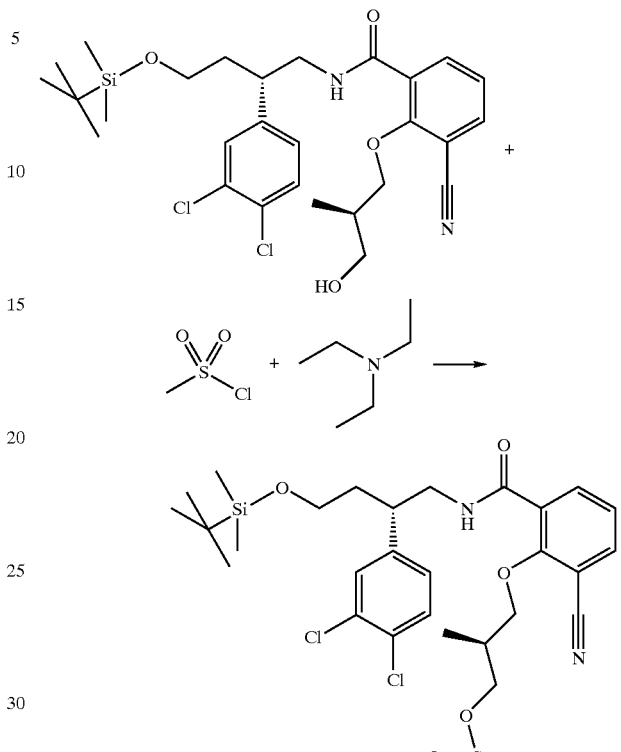

N-[4-(tert-Butyldimethylsilanyloxy)-2-(S)-(3,4-dichlorophenyl)butyl]-3-cyano-2-(3-methylsulfonyloxy-2-(R)-methylpropoxy)benzamide. To a stirred, cooled (ice-bath, 0°) solution of N-[4-(tert-butyldimethylsilanyloxy)-2-(S)-(3,4-dichlorophenyl)butyl]-3-cyano-2-(3-hydroxy-2-(R)-methylpropoxy)benzamide (4.64 g, 8.2 mmol) and triethylamine (1.74 mL, 12.5 mmol) in 72 mL of DCM was added methanesulfonyl chloride (0.71 mL, 9.2 mmol) dropwise by syringe. The mixture was stirred in the ice bath and allowed to warm to RT overnight. After 60 hr the reaction mixture was partitioned between water and DCM, the layers separated and the organic layer washed twice with portions of dilute HCl and sat. NaHCO₃, dried (Na₂SO₄), filtered and the solvent removed in vacuo. Chromatography with 8:2, 4:6, and 1:9 hexane:Et₂O and 7:3 DCM:Et₂O as eluent returned the title compound as a colorless gum, 5.02 g (95%). MS APCI, m/z=643 (M+1).

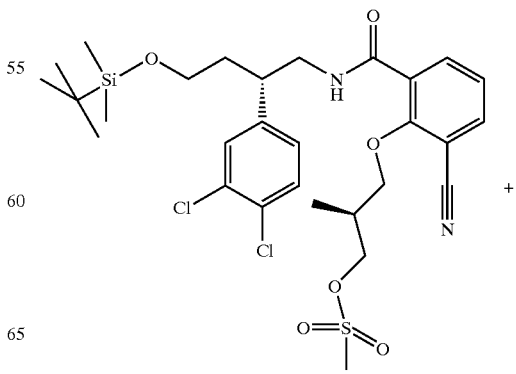

-continued

Na—H →

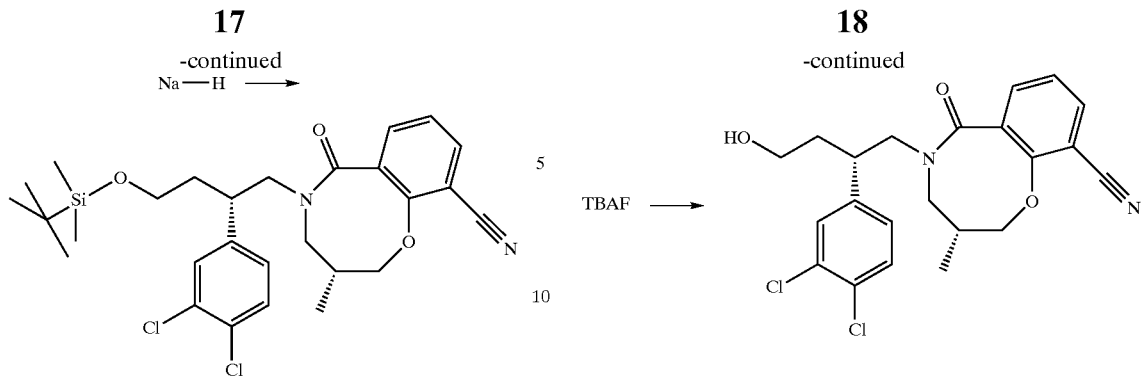

5-[4-(tert-Butyldimethylsilanyloxy)-2-(S)-(3,4-dichlorophenyl)butyl]-10-cyano-3-(R)-methyl-6-oxo-3,4,5,6-tetrahydro-2H-benzo[b][1,5]oxazocine.

A solution of N-[4-(tert-butyldimethylsilanyloxy)-2-(S)-(3,4-dichlorophenyl)butyl]-3-cyano-2-(3-methylsulfonyloxy-2-(R)-methylpropoxy)benzamide (5.02 g, 7.8 mmol) in DMF (100 mL) was added dropwise to a stirred slurry of 60% NaH (0.33 g, 8.2 mmol) in DMF (50 mL). The mixture was placed in an oil bath at 65° C. and stirred at that temperature for 1 hr. The cooled reaction mixture was treated with DCM, water and sat. NH$_4$Cl, stirred 10 min and the layers separated. The organic phase was washed twice with water, dried (Na$_2$SO$_4$), filtered and the solvent removed in vacuo. Chromatography with 8:2, 7:3 and 1:1 hexane:Et$_2$O as eluent returned 1.0 g (23%) of the title compound as a white solid. $^1$H NMR (300 MHz, CDCl$_3$) δ 7.59 (bd, 1H), 7.39 (d, 1H), 7.29 (s, 2H), 7.12 (d, 1H), 7.00 (t, 1H), 4.33–4.66 (m, 2H), 4.10 (dd, 1H), 3.13–3.63 (m, 6H), 1.76–2.14 (m, 3H), 1.12 (br d, 3H), 0.89 (s, 9H), 0.01 (s, 3H), 0.00 (s, 3H). MS APCI, m/z=547 (M+1).

Also obtained was 1.93 g (45%) of N-[4-(tert-butyldimethylsilanyloxy)-2-(S)-(3,4-dichlorophenyl)butyl]-3-cyano-2-(2-methylallyloxy)benzamide as a colorless gum. $^1$H NMR (300 MHz, CDCl$_3$) δ 8.33 (d, 1H), 7.12 (d, 1H), 7.59 (br s, 1H), 7.30–7.42 (m, 3H), (7.07 9d, 1H), 5.04 (br s, 2H), 4.47 (s, 2H), 0.88 (s, 9H), 0.00–0.02 (m, 6H). MS APCI, m/z=547 (M+1).

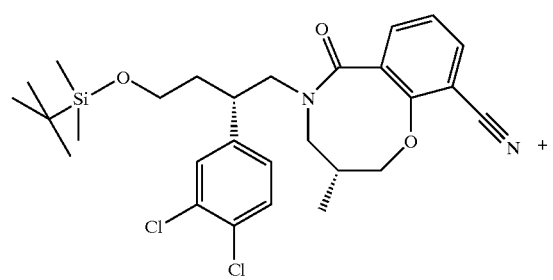

TBAF →

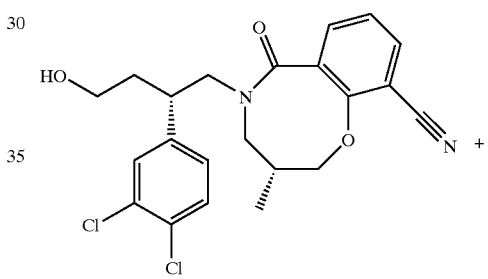

5-[4-Hydroxy-2-(S)-(3,4-dichlorophenyl)butyl]-10-cyano-3-(R)-methyl-6-oxo-3,4,5,6-tetrahydro-2H-benzo[b][1,5]oxazocine. A 1.0 M solution of tetrabutylammonium fluoride in THF (2.2 mL, 2.2 mmol) was added to a stirred solution of 5-[4-(tert-butyldimethylsilanyloxy)-2-(S)-(3,4-dichlorophenyl)butyl]-10-cyano-3-(R)-methyl-6-oxo-3,4,5,6-tetrahydro-2H-benzo[b][1,5]oxazocine (1.00 g, 1.83 mmol) and THF (20 mL) and the mixture stirred at ambient temperature for 3.5 hr. The mixture was partitioned between DCM and water, the organic layer collected, washed with water, dried (Na$_2$SO$_4$), filtered and the solvent removed in vacuo. The white solid was dried under high vacuum overnight to yield 0.76 g (96%) of the title compound. $^1$H NMR (300 MHz, CDCl$_3$) δ 7.59 (d, 1H), 7.26–7.40 (m, 3H), 6.98–7.12 (m, 2H), 4.38 (br s, 2H), 4.07 (dd, 1H), 3.13–3.69 (m, 6H), 1.80–2.05 (m, 3H), 1.61 (br s, 1H), 1.01–1.08 (m, 3H). MS APCI, m/z=433 (M+1).

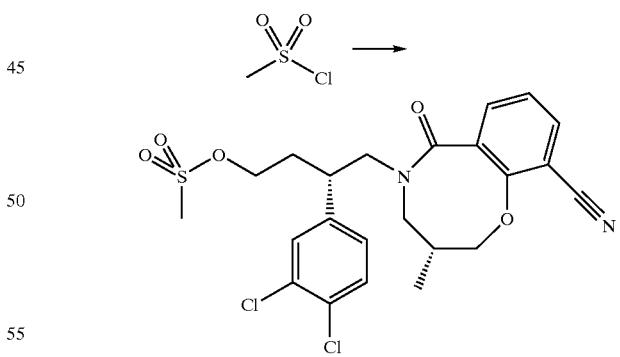

5-[4-Methylsulfonyloxy-2-(S)-(3,4-dichlorophenyl)butyl]-10-cyano-3-(R)-methyl-6-oxo-3,4,5,6-tetrahydro-2H-benzo[b][1,5]oxazocine. To a stirred cooled (0° C., ice-bath) solution of 5-[4-hydroxy-2-(S)-(3,4-dichlorophenyl)butyl]-10-cyano-3-(R)-methyl-6-oxo-3,4,5,6-tetrahydro-2H-benzo[b][1,5]oxazocine (0.35 g, 0.81 mmol) and triethylamine (0.184 mL, 1.32 mmol) in DCM (8 mL) was added, dropwise from a pipette, methanesulfonyl chloride (0.076 mL, 0.97 mmol) and the mixture allowed to stir in the bath and warm to RT. After 3 hr the reaction mixture was added to a 10 g Mega-Bond Elut® column, eluted with an additional 50 mL of DCM (discarded) and then 10% Et$_2$O in DCM. The first 100 mL of the 10% Et$_2$O in DCM eluent was stripped in vacuo to yield the title compound as a white foam (0.44 g, quantitative). $^1$H NMR (300 MHz, CDCl$_3$) δ 7.59 (d, 1H), 7.42 (d, 1H), 7.26–7.31 (m, 2H), 6.98–7.13 (m, 2H), 3.99–4.48 (m, 5H), 2.97 (s, 3H). MS APCI, m/z=511 (M+1).

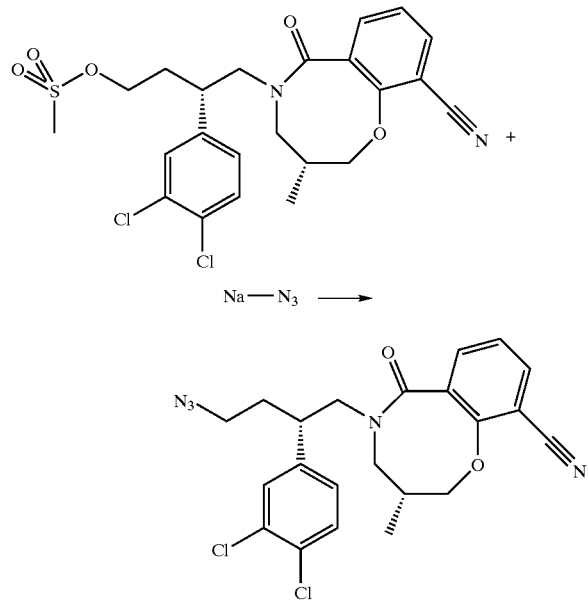

5-[4-Azido-2-(S)-(3,4-dichlorophenyl)butyl]-10-cyano-3-(R)-methyl-6-oxo-3,4,5,6-tetrahydro-2H-benzo[b][1,5]oxazocine. To a stirred solution of 5-[4-methylsulfonyloxy-2-(S)-(3,4-dichlorophenyl)butyl]-10-cyano-3-(R)-methyl-6-oxo-3,4,5,6-tetrahydro-2H-benzo[b][1,5]oxazocine (above crude, 0.81 mmol) in DMF (4 mL) was added sodium azide (0.137 g, 2.04 mmol) and the mixture stirred at RT overnight. The mixture was added to water (100 mL) and extracted twice with DCM. The solvent was stripped from the combined organic layer and the residue was dissolved in EtOAc (40 mL), washed with brine (4×100 mL), dried (MgSO$_4$) filtered and the solvent removed in vacuo to yield the title compound as a solid foam, 0.37 g (quantitative). $^1$H NMR (300 MHz, CDCl$_3$) δ 7.59 (dd, 1H), 7.41 (d, 1H), 7.30 (br s, 2H), 6.98–7.11 (m, 2H), 4.38 (br s, 2H), 4.11 (m, 1H), 3.05–3.34 (m, 5H), 1.81–2.09 (m, 3H), 1.11 (br s, 2H). MS APCI, m/z=458 (M+1).

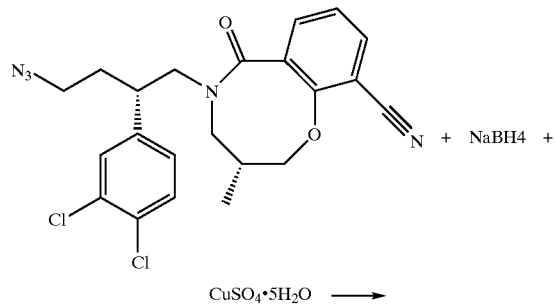

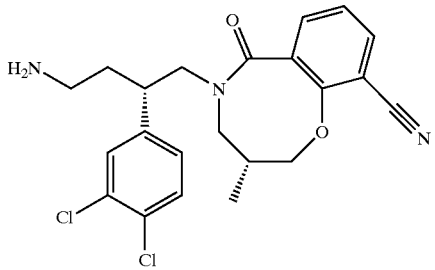

5-[4-Amino-2-(S)-(3,4-dichlorophenyl)butyl]-10-cyano-3-(R)-methyl-6-oxo-3,4,5,6-tetrahydro-2H-benzo[b][1,5]oxazocine. The following is a modification of the method of Rao and Siva, Synth. Commun. 24(4) 549 (1994). To a stirred cooled (ice-bath) mixture of 5-[4-azido-2-(S)-(3,4-dichlorophenyl)butyl]-10-cyano-3-(R)-methyl-6-oxo-3,4,5,6-tetrahydro-2H-benzo[b][1,5]oxazocine (the above crude, 0.81 mmol), copper(II) sulfate (0.026 g, 0.10 mmol) and MeOH (2 mL) was added sodium borohydride (0.31 g, 8.2 mmol) in one portion and the mixture stirred at RT overnight. Some starting mesylate remained as shown by TLC (silica gel, 2% MeOH/DCM) so that the mixture was re-cooled in an ice-bath and additional NaBH$_4$ (0.175 g, 4.6 mmol) added. After stirring 2 hr in the ice-bath and 3 hr at ambient temperature 1N NaOH was added to achieve pH 12 and the mixture partitioned between water and DCM. The organic layer was collected, washed twice with water, dried (Na$_2$SO$_4$), filtered and the solvent stripped in vacuo. Chromatography using 5%, 10% and 20% MeOH/DCM as eluent returned the title compound as a white solid (0.24 g, 69%); converted to the citrate salt, mp 82–128° C. Calcd for C$_{22}$H$_{23}$Cl$_2$N$_3$O$_2$·C$_6$H$_8$O$_7$·H$_2$O: C, 52.34; H, 5.18; N, 6.54. Found: C, 52.21; H, 5.13; N, 6.26. $^1$H NMR (300 MHz, CDCl$_3$) δ 7.58 (d, 1H), 7.38 (d, 1H), 7.26–7.33 (m, 2H), 7.06–7.15 (br m, 1H) 7.00 (t, 1H), 4.26–4.55 (br m, 2H), 4.07 (dd, 1H). MS APCI, m/z=432 (M+1).

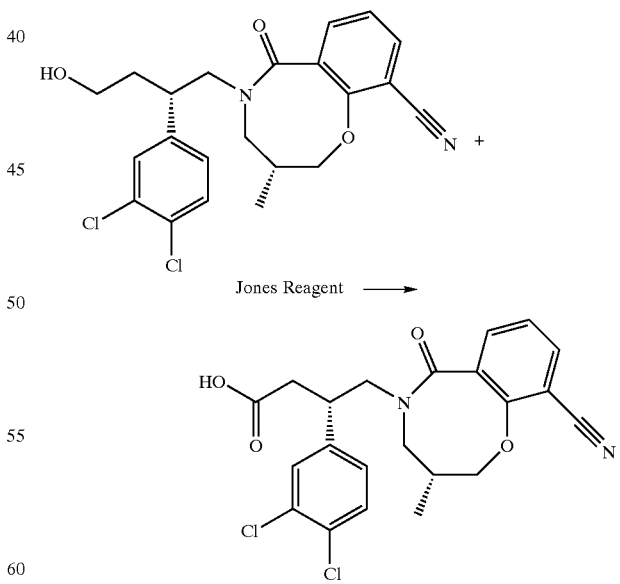

5-[3-Carboxy-2-(S)-(3,4-dichlorophenyl)propyl]-10-cyano-3-(R)-methyl-6-oxo-3,4,5,6-tetrahydro-2H-benzo[b][1,5]oxazocine. To a cooled (ice-bath, 0° C.) stirred mixture of Jones Reagent [0.60 mL of a solution prepared from CrO$_3$ (2.73 g, 27.3 mmol), $H_2SO_4$ (2.3 mL) and water (10.0 mL)] and acetone (10 mL) was added dropwise a solution of 5-[4-hydroxy-2-(S)-(3,4-dichlorophenyl)butyl]-10-cyano-3-(R)-methyl-6-oxo-3,4,5,6-tetrahydro-2H-benzo[b][1,5]oxazocine (0.329 g, 0.76 mmol) and 14 mL of acetone. After stirring 2 hr at RT the reaction was quenched by the dropwise addition of i-PrOH until a blue color persisted (~3 mL). After 15 min the reaction mixture was partitioned between DCM and water, the organics separated, washed with water, dried ($Na_2SO_4$), filtered and the solvent stripped in vacuo. Chromatography using 5%, 10% and 20% MeOH/DCM as eluent returned the title compound as a white solid (0.326 g, 96%). $^1$H NMR (300 MHz, DMSO-$d_6$) δ 12.10 (s, 1H), 7.80 (dd, 1H), 7.50–7.56 (m, 2H), 7.28 (dd, 1H), 7.17 (br s, 1H), 7.10 (t, 1H). MS APCI, m/z=447 (M+1), 445 (M–1).

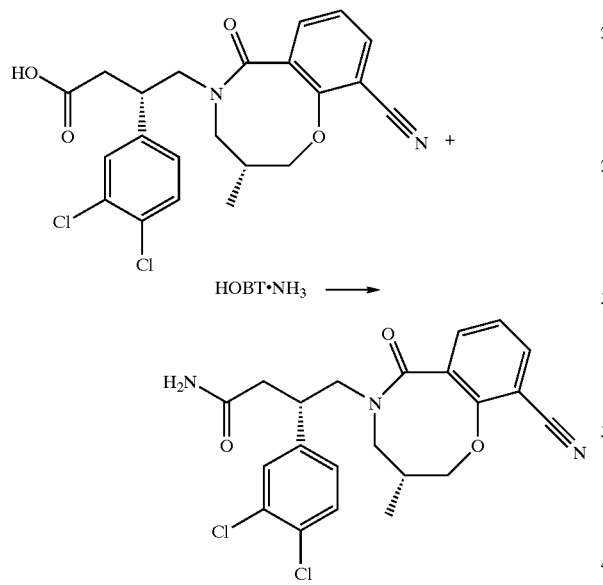

5-[3-Aminocarbonyl-2-(S)-(3,4-dichlorophenyl)propyl]-10-cyano-3-(R)-methyl-6-oxo-3,4,5,6-tetrahydro-2H-benzo[b][1,5]oxazocine. To a stirred solution of 5-[3-carboxy-2-(S)-(3,4-dichlorophenyl)propyl]-10-cyano-3-(R)-methyl-6-oxo-3,4,5,6-tetrahydro-2H-benzo[b][1,5]oxazocine (0.326 g, 0.73 mmol) and DMF (8 mL) was added HOBt·NH$_3$ (0.273 g, 1.80 mmol) and 1-[3-(dimethylaminopropyl]-3-ethylcarbodiimide hydrochloride (0.287 g, 1.50 mmol) and the mixture stirred at RT overnight. The reaction mixture was treated with sat NaHCO$_3$, DCM and a large volume of water. The organics were collected, washed twice with a large volume of water, dried (Na$_2$SO$_4$), filtered and the solvent stripped in vacuo. Chromatography using 0.5%, 1%, 2% and 5% MeOH/DCM as eluent returned 0.240 g (78%) of the title compound as a white solid, mp 92–144°. Calc'd for $C_{22}H_{21}Cl_2N_3O_3·H_2O$: C, 60.70; H, 4.89; N, 8.16. Found: C, 60.73, H, 4.71; N, 7.53. $^1$H NMR (300 MHz, CDCl$_3$) δ 8.15 (s, 1H), 7.74 (dd, 1H), 7.42–7.47 (m, 3H), 7.24–7.27 (m, 1H), 6.71–6.74 (m, 1H), 5.56 (br s, 1H), 5.32 (br s, 1H), 4.80 (t, 1H), 4.65 (dd, 1H), 3.80 (q, 1H), 3.57–3.67 (m, 1H), 3.23–3.30 (m, 3H), 2.55–2.71 (m, 2H), 2.29–2.39 (m, 1H), 1.21 (t, 1H), 0.98 (d, 3H). MS APCI, m/z=446 (M+1).

What is claimed is:

1. A compound having the formula

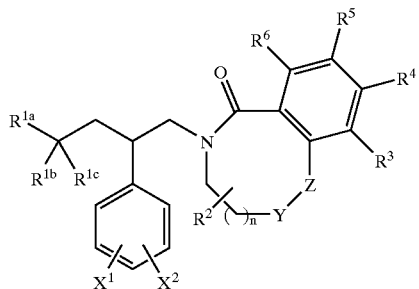

wherein:

$R^{1a}$ is H, $NR^9R^{10}$, —$OR^9$,

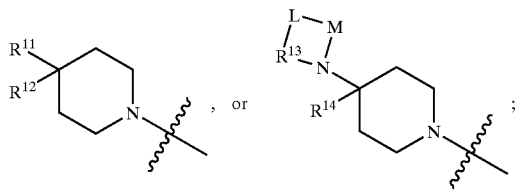

$R^{1b}$ and $R^{1c}$ are independently H or —$OR^9$, or $R^{1b}$ and $R^{1c}$ together are =O, =CH$_2$ or —OCH$_2$CH$_2$O—;

$R^2$ is H, oxo, —$OR^9$ or —CH$_3$;

$R^3$, $R^4$, $R^5$ and $R^6$ are each independently selected from H, cyano, nitro, trifluoromethoxy, trifluoromethyl, $C_{1-6}$alkylsulfonyl, halo, —$OR^9$, —OCH$_2$O—, $C_{1-6}$alkyl, $C_{2-6}$alkenyl, $C_{2-6}$alkynyl, —C(=O)$OR^9$, —C(=O)$NR^9R^{10}$, —OC(=O)$R^9$, —$NR^9$C(=O)$R^{10}$, aminosulfonyl and $C_{1-6}$alkyl substituted by cyano, nitro, trifluoromethoxy, trifluoromethyl, $C_{1-6}$alkylsulfonyl, halo, —$OR^9$, —OCH$_2$O—, $C_{1-6}$alkyl, $C_{2-6}$alkenyl, $C_{2-6}$alkynyl, —C(=O)$OR^9$, —C(=O)$NR^9R^{10}$, —OC(=O)$R^9$, —$NR^9$C(=O)$R^{10}$, or aminosulfonyl; wherein at least one of $R^3$, $R^4$, $R^5$ and $R^6$ are H;

$R^9$ and $R^{10}$ are each independently H or $C_{1-6}$alkyl;

$R^{11}$ is phenyl, substituted in at least the ortho position by $C_{1-6}$alkylthio, $C_{1-6}$alkylsulfinyl, $C_{1-6}$alkylsulfonyl, trifluoromethylthio, trifluoromethylsulfinyl, $C_{1-6}$alkanesulfonamido, $C_{1-6}$alkanoyl, $C_{1-6}$alkoxycarbonyl, succinamido, carbamoyl, $C_{1-6}$alkylcarbamoyl, di-$C_{1-6}$alkylcarbamoyl, $C_{1-6}$alkoxy-$C_{1-6}$alkylcarbamoyl, N-methylcarbamoyl, $C_{1-6}$alkanoylamino, ureido, $C_{1-6}$ureido, di-$C_{1-6}$alkylureido, amino, $C_{1-6}$alkylamino, or di-$C_{1-6}$alkyamino;

$R^{12}$ is selected from hydrogen, hydroxy, $C_{1-6}$alkoxy, $C_{1-6}$alkanoyloxy, $C_{1-6}$alkanoyl, $C_{1-6}$alkoxycarbonyl, $C_{1-6}$alkanoylamino, $C_{1-6}$alkyl, carbamoyl, $C_{1-6}$alkylcarbamoyl and bis($C_{1-6}$alkyl)carbamoyl;

$R^{13}$ is —CH$_2$CH$_2$—, —CH$_2$CH$_2$CH$_2$— or —CH$_2$CH$_2$CH$_2$CH$_2$—;

$R^{14}$ is hydrogen, hydroxy, $C_{1-6}$alkoxy, $C_{1-6}$alkanoyloxy, $C_{1-6}$alkanoyl, $C_{1-6}$alkoxycarbonyl, $C_{1-6}$alkanoylamino, $C_{1-6}$alkyl, carbamoyl, $C_{1-6}$alkylcarbamoyl or di-$C_{1-6}$alkylcarbamoyl;

M is —C(=O)— or —S(=O)$_2$—;

L is —NH— or —CH$_2$—;

$X^1$ and $X^2$ are independently H or halogen, wherein at least one of $X^1$ and $X^2$ are halogen;

Y and Z are CH$_2$ or O, wherein Y does not equal Z;

n is 0 or 1; and any pharmaceutically-acceptable salt thereof.

2. A compound according to claim 1 wherein $R^3$, $R^4$, $R^5$ and $R^6$ are selected from H, cyano, nitro, —S(=O)$C_{1-6}$alkyl, halo, —OR$^9$, —OCH$_2$O—, $C_{1-6}$alkyl, $C_{2-6}$alkenyl, $C_{2-6}$alkynyl, —C(=O)OR$^9$, —C(=O)NR$^9$R$^{10}$, —OC(=O)R$^9$, —NR$^9$C(=O)R$^{10}$, aminosulfonyl and —$C_{1-6}$alkyleyano; wherein at least two of $R^3$, $R^4$, $R^5$ and $R^6$ are H.

3. A compound according to claim 1 wherein $R^3$, $R^4$, $R^5$ and $R^6$ are selected from H, cyano, methoxy, ethoxy, isopropoxy, fluoro, bromo, chloro, iodo, nitro, cyanomethyl, carboxy, carbamoyl, ethynyl, methyl, ethyl, dimethylcarbomoyl, methylsulfonyl, aminosulfonyl, prop-2-enyl, acetyl and acetylamino; wherein at least two $R^3$, $R^4$, $R^5$ and $R^6$ are H.

4. A compound according to claim 1 wherein $R^3$, $R^4$, $R^5$ and $R^6$ are selected from H, cyano, methoxy, ethyl, fluoro and nitro; wherein at least two of $R^3$, $R^4$, $R^5$ and $R^6$ are H.

5. A compound according to claim 1 wherein:
$R^{1a}$ is

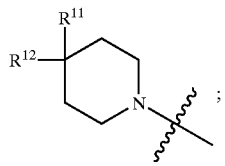

$R^{1b}$ is H; and
$R^{1c}$ is H.

6. A compound according to claim 1 wherein:
$R^{1a}$ is

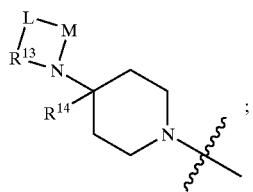

$R^{1b}$ is H; and
$R^{1c}$ is H.

7. A compound according to claim 1 wherein:
$R^{1a}$ is H, NR$^9$R$^{10}$ or —OR$^9$.

8. A compound according to claim 1 wherein:
$R^2$ is —OR$^5$ or —CH$_3$.

9. A pharmaceutical composition comprising a therapeutically-effective amount of a compound according to claim 1.

* * * * *